United States Patent
Shevitz

(10) Patent No.: US 6,544,424 B1
(45) Date of Patent: Apr. 8, 2003

(54) FLUID FILTRATION SYSTEM

(75) Inventor: Jerry Shevitz, Livingston, NJ (US)

(73) Assignee: Refined Technology Company, East Hanover, NJ (US)

( * ) Notice: Subject to any disclaimer, the term of this patent is extended or adjusted under 35 U.S.C. 154(b) by 0 days.

(21) Appl. No.: 09/527,426

(22) Filed: Mar. 17, 2000

Related U.S. Application Data

(60) Provisional application No. 60/168,878, filed on Dec. 3, 1999.

(51) Int. Cl.⁷ .............................................. B01D 61/00
(52) U.S. Cl. .................. 210/650; 210/636; 210/326.69; 210/257.2; 210/195.2; 210/321.8
(58) Field of Search ........................... 210/257.2, 195.2, 210/321.79, 321.8, 636, 321.69, 650

(56) References Cited

U.S. PATENT DOCUMENTS

| | | | |
|---|---|---|---|
| 3,505,215 A | * | 4/1970 | Bray |
| 4,592,848 A | | 6/1986 | Pabst .......................... 210/798 |
| 4,643,715 A | | 2/1987 | Isono et al. ..................... 604/4 |
| 4,844,804 A | * | 7/1989 | Taylo |
| 5,006,234 A | * | 4/1991 | Menon et al. |
| 5,234,605 A | | 8/1993 | Reipur et al. ................ 210/741 |
| 5,354,466 A | * | 10/1994 | Yumoki |
| 5,468,387 A | * | 11/1995 | Solomon |
| 5,516,431 A | | 5/1996 | Kawamura et al. ......... 210/645 |
| 5,527,467 A | | 6/1996 | Ofsthun et al. ............. 210/645 |
| 5,690,829 A | * | 11/1997 | Lauer |
| 5,911,884 A | * | 6/1999 | Boulter |
| 6,001,244 A | * | 12/1999 | Salter et al. |

* cited by examiner

Primary Examiner—Ana Fortuna
(74) Attorney, Agent, or Firm—Roberts & Mercanti, LLp

(57) ABSTRACT

A filtration systems for fluids, particularly biological fluids. The filtration system includes a filter containing compartment connected at one end to a storage vessel and at the other end to a diaphragm pump. The filter comprises a hollow fiber module or a screen filter. The vessel serves as a storage container for a process stream to be filtered. The diaphragm pump provides the means for generating rapid, alternating, low shear tangential flow between the vessel and pump and through the hollow fibers or screen filter. The system allows easy removal of wastes from the fluid and the addition of fresh fluid to replenish the filtered fluid.

31 Claims, 3 Drawing Sheets

FLUID FILTRATION SYSTEM

CROSS REFERENCE TO RELATED APPLICATION

This application claims the benefit of copending U.S. provisional application serial No. 601168,878 filed Dec. 3, 1999 which is incorporated herein by reference.

BACKGROUND OF THE INVENTION

1. Field of the Invention

The present invention relates to filtration systems. More specifically, the invention relates to a filtration system for fluids, particularly biological fluids. The filtration system includes a filter containing compartment connected at one end to a storage vessel and at the other end to a diaphragm pump. The system creates an alternating tangential flow of fluid through a filter element, a process that offers the benefits of tangential flow without some of its drawbacks. As will become apparent, some of the benefits not offered by other systems include improved processing of fragile materials such as animal cells and biomolecules. Other benefits of the system are embodied in the closed nature of the invention, which among other things allows simplified sanitation and sterilization of the system and allows confinement of biological or some other hazardous material for protection against contamination. Yet other benefits include extended filter life with applications in long term filtration processes such as perfusion of animal cells. Waste fluids may be removed from the culture by filtration, as desired, and fresh fluid may be added to replenish the filtered fluid.

2. Description of the Related Art

Filtration is typically performed to separate, clarify, modify and/or concentrate a fluid solution, mixture or suspension. In the biotechnology and pharmaceutical industries, filtration is vital for the successful production, processing, and testing of new drugs, diagnostics and other biological products. For example, in the process of manufacturing biologicals, using animal cell culture, filtration is done for clarification, selective removal and concentration of certain constituents from the culture media or to modify the media prior to further processing. Filtration may also be used to enhances productivity by maintaining a culture in perfusion at high cell concentration. The invention provides an improved means for fractionating a mixture or suspension of molecules or particulates based on physical and/or chemical properties.

Several specialized filters and filtration methods have been developed to separate materials according to their chemical and physical properties. Filters which have been developed in the art include flat surface filters, pleated filters, multi-unit cassettes, and tubular forms such as hollow fibers. However, many of these filters have short operating lives, and when used to filter cell culture suspension or other biological fluids they tend to clog with dead cells, cell debris, aggregates or other constituents of the fluid. In this regard, U.S. Pat. No. 5,527,467 describes a bioreactor having a one-way rectifying membrane which reduces back filtration of solute molecules.

Sensitivity of many culture media to heat and chemical sterilization precludes the use of some filtration methods. U.S. Pat. No. 4,643,715 describes a medical permeating membrane through which bodily fluids flow in dialysis. U.S. Pat. No. 5,516,431 shows a plasma filtration process for separating blood into blood cells and plasma and the removal of harmful macromolecules. None of the above patents shows filtering with backflushing. U.S. Pat. No. 4,592,848 shows a flow through filter with backflush clearing capability, however, no diaphragm pump is used. U.S. Pat. No. 5,234,605 shows filtering with backflush clearing capability using a diaphragm pump, however, fluids do not traverse back and forth between a fluid storage vessel and a diaphragm pump via an intermediate filter.

Animal cells grow substantially slower than most microorganisms, and lacking protective cell wall, they are also more fragile. Some known methods for increasing the productivity of microbial culture production including increasing agitation rates and vigorous delivery of gases into the culture are not feasible with animal cells. Thus, production is limited to very gentle culture conditions and low cell concentrations. One way to increase the cell concentration, yet maintain gentle culture conditions is through the perfusion method.

In the perfusion method for growing cells, culture medium, whose nutrients have been consumed and which contains increased levels of harmful waste products, is continuously removed from the culture and replaced with fresh medium. The constant addition of fresh medium while eliminating waste products provides the cells with the nutrients it requires to achieve high cell concentrations. Unlike the constant changing conditions during batch culture method of production, the perfusion method offers the means to achieve and maintain a culture in steady state.

In normal batch cultures production processes, cells are first inoculated into a fresh medium and the cells rapidly enter a log grow phase. As they consume the medium nutrients and waste products accumulate, the cells transition to a stationary followed by a decay phase. While several methods have been developed to optimize batch culture production, in each case, these processes undergo rapid growth and decay cycles. In perfusion, however, since waste products generated by the culture are continuously removed and the culture is continuously replenished with fresh medium, it is possible to achieve a state of equilibrium in which cell concentration and productivity are maintained. Typically, about one culture volume is exchanged per day and the cell concentration achieved in perfusion are typically 2 to more than 10 times that achieved at the peak of batch culture.

Despite the potential benefits of the perfusion method, it has gained only modest acceptance. One key reason is due to the low reliability of currently available perfusion devices. Presently known perfusion methods which are used to separate a medium from cells frequently damage the cells. This damage may result from direct physical disruption by shearing forces of the system, depletion of nutrients in the medium, changes in physiological conditions of the culture, such as ionic strength, pH, etc., exposure to growth suppressing elements released by the cells. The resulting build up of dead cells and aggregates on screens or filters, resulting in clogging and failure of the perfusion device. At high cell concentrations, typical of perfusion cultures, these problems may be amplified. This is particularly the case with a number of perfusion devices which are contained inside the process vessel and can not be replaced during a production run. Should such an internal system fail, the entire production run must terminated.

The "spin basket" system is one type of internal perfusion device. This method uses a basket, which may contain an agitation impeller on the bottom center axis. The perimeter surface of the basket is covered by a mesh screen, with about 20 micron pore opening. Rotation of the basket inhibits the attachment of cells to the screen or penetration through the screen into the basket. Waste medium removed from within the basket is replaced by addition of fresh medium to the culture. This system is limited, however, because cells and cell debris gradually do accumulate on the screen, reducing the screen's ability to fractionate the cells from the medium. Eventually insufficient medium can be removed from the system to maintain an adequate perfusion rate. The culture deteriorate as it becomes increasingly deprived of nutrients.

The use of flat filters and "plate and frame" systems have limited usefulness in perfusion applications since such systems are difficult to sterilize or keep sterile. Furthermore, maintaining uniform flow across the entire rectangular cross section of the filter is somewhat difficult. Other perfusion devices based on cell settling have not been used extensively because of limited scale up potential and the nonhomogeneous nature of the settling device. Cells confined to the settling device may be deprived of essential nutrients, primarily oxygen.

In one type of external filtration perfusion systems, a culture medium is circulated from a vessel, through a hollow fiber cartridge and back to the vessel. A pump attached to the tubing between hollow fiber and vessel circulates the culture content from the vessel, through the hollow fiber cartridge and back to the vessel. The process produces tangential flow across the hollow fiber membranes. A second pump on the filtrate side of the hollow fiber cartridge controls the rate of filtrate removal. The use of hollow fiber is preferred over flat sheet, plate and frame, type systems because, unlike the later, the enclosed nature of the hollow fiber module is simpler to sterilize and maintain sterile, uniform flow can be generated across the entire cross section of the hollow fiber module. One may also achieve uniform scale-up by a proportional increase in the number of hollow fibers. However, like the spin-basket method, the hollow fiber filters are prone to clogging by accumulation of particulates and gelatin on the membrane surface. Recirculation in one direction through the hollow fiber cartridge typically results in clogging of the hollow fiber lumen by aggregates lodging at lumen inlet. Such aggregates may grow in size and as more hollow fibers are blocked, filtration capacity declines.

It would therefore be desirable to create a filtration system where waste medium or fluid is continuously removed and the fluid is continuously replenished with fresh medium. It would also be desirable to create a filtration system which creates an alternating tangential flow which continuously filters fluids, such as biological fluids with minimal damage to cells or other constituents of a particular process, which minimizes clogging, that may be replaced in mid process with minimum disruption of the process, that may be sterilized in all parts and maintain sterile, that may contain only a single connection to the process vessel and that may be adaptable to most process.

The present invention provides a solution to these problems. It includes a filter containing compartment connected at one end to a storage vessel and at the other end to a diaphragm pump. The pump circulates a fluid from the vessel through the filter element and to the pump. The flow is then reversed, and the fluid is circulated back from the pump through the filter element and to the vessel. Thus, an alternating tangential flow of fluid is produced across the filter element. Furthermore, uniform flow can be generated across the entire filter. Thus, this system thus provides a means for generating rapid, low shear, tangential flow. The process is also advantageous for maintaining since the system can be sterilized without terminating a production run. Hollow fiber (HF) type filters afford longer operating lives, and they are available in many sizes, configurations, materials, pore sizes and porosity. Furthermore, the process need not be limited to the use of hollow fiber filters. It is possible to insert other separation devices in the hollow fiber housing. One such device is screen module, consisting of a screen mash as the separation matrix. All such separation modules will be referred to, collectively, as the filter element or simply as the filter. Additional advantages not offered by other filtration systems will become apparent to those skilled in the art upon a consideration of the configuration to be described.

SUMMARY OF THE INVENTION

The invention provides a fluid filtration system comprising:

a) at least one fluid storage vessel;

b) at least one filter containing compartment;

c) a fluid connector attached to the storage vessel and to an entrance end of the filter containing compartment, which connector is capable of directing a fluid from the storage vessel into the entrance end of the filter containing compartment;

d) at least one diaphragm pump connected at an exit end of the filter containing compartment; which diaphragm pump is capable of alternately receiving fluid from the exit end of the filter containing compartment and then expelling the fluid back into the exit end of the filter containing compartment; and e) at least one fluid harvest port connected to the filter containing compartment for removing filtered fluid from the filter containing compartment.

The invention further provides a process for filtering a fluid comprising:

a) providing a fluid filtration system comprising at least one fluid storage vessel;

at least one filter containing compartment; a fluid connector attached to the storage vessel and to an entrance end of the filter containing compartment, which connector is capable of directing a fluid from the storage vessel into the entrance end of the filter containing compartment;

at least one diaphragm pump connected at an exit end of the filter containing compartment; which diaphragm pump is capable of alternately receiving fluid from the exit end of the filter containing compartment and then expelling the fluid back into the exit end of the filter containing compartment; and at least one fluid harvest port connected to the filter containing compartment for removing filtered fluid from the filter containing compartment;

b) filtering a fluid by causing the fluid to flow from the storage vessel through the filter containing compartment and then to the diaphragm pump;

c) re-filtering the fluid by causing at least a portion of the fluid to flow from the diaphragm pump through the filter containing compartment and then to the storage vessel;

d) optionally repeating steps b and c; and e) removing the filtered fluid from the filtration system.

The invention also provides a process for sterilizing a fluid filtration system comprising:

a) providing a fluid filtration system comprising at least one fluid storage vessel;

at least one filter containing compartment; a fluid connector attached to the storage vessel and to an entrance end of the filter containing compartment, which connector is capable of directing a fluid from the storage vessel into the entrance end of the filter containing compartment;

at least one diaphragm pump connected at an exit end of the filter containing compartment; which diaphragm pump is capable of alternately receiving fluid from the exit end of the filter containing compartment and then expelling the fluid back into the exit end of the filter containing compartment; and at least one fluid harvest port connected to the filter containing compartment for removing filtered fluid from the filter containing compartment;

b) injecting steam into at least a portion of the fluid filtration system via at least one steam inlet; and c) removing the steam from the fluid filtration system via at least one steam outlet.

The invention still further provides a fluid filtration system comprising:

a) at least one fluid storage vessel;

b) at least one filter containing compartment;

c) a fluid connector attached at one end thereof to the storage vessel by a valve, and attached at another end thereof to an entrance end of the filter containing compartment by a valve, which connector is capable of directing a fluid from the storage vessel into the entrance end of the filter containing compartment; said fluid connector having a steam injection port and a condensate outlet;

d) at least one diaphragm pump connected at an exit end of the filter containing compartment; which diaphragm pump is capable of alternately receiving fluid from the exit end of the filter containing compartment and expelling the fluid back into the exit end of the filter containing compartment; said diaphragm pump having a pump housing comprising a first and a second chamber separated by a diaphragm; the first chamber of the diaphragm pump being connected to a gas port capable of alternately injecting a gas into and out of the first chamber; the second chamber being in fluid flow cooperation with the exit end of the filter containing compartment; a controller for controlling the movement of the diaphragm within the pump housing; a fluid sampling port attached through a wall of the second chamber;

e) at least one fluid harvest port connected to the filter containing compartment for removing filtered fluid from the filter containing compartment, said harvest port being connected via a fluid flow line to a fluid pump; first and second fluid control valves attached in series between the harvest port and the fluid pump; a steam injection port and a condensate outlet attached to the fluid flow line between the steam injection port and a condensate outlet;

f) a pressure dampener attached through a wall of the filter containing compartment;

g) wherein the filter which comprises a plurality of bundled hollow fibers whose axes extend longitudinally from the entrance end to the exit end of the filter containing compartment.

DETAILED DESCRIPTION OF THE PREFERRED EMBODIMENT

The present invention concerns a fluid filtration system generally comprising at least one fluid storage vessel, a fluid connector for directing fluid from the vessel through a filter containing compartment, at least one diaphragm pump which powers the fluid in alternating directions through the filter containing compartment, and at least one fluid harvest port. The system is useful for conducting a rapid, low sheer, tangential flow filtration. Such a system has applications in perfusion of cultured animal cells as well as other varied filtration applications.

Figure 1:
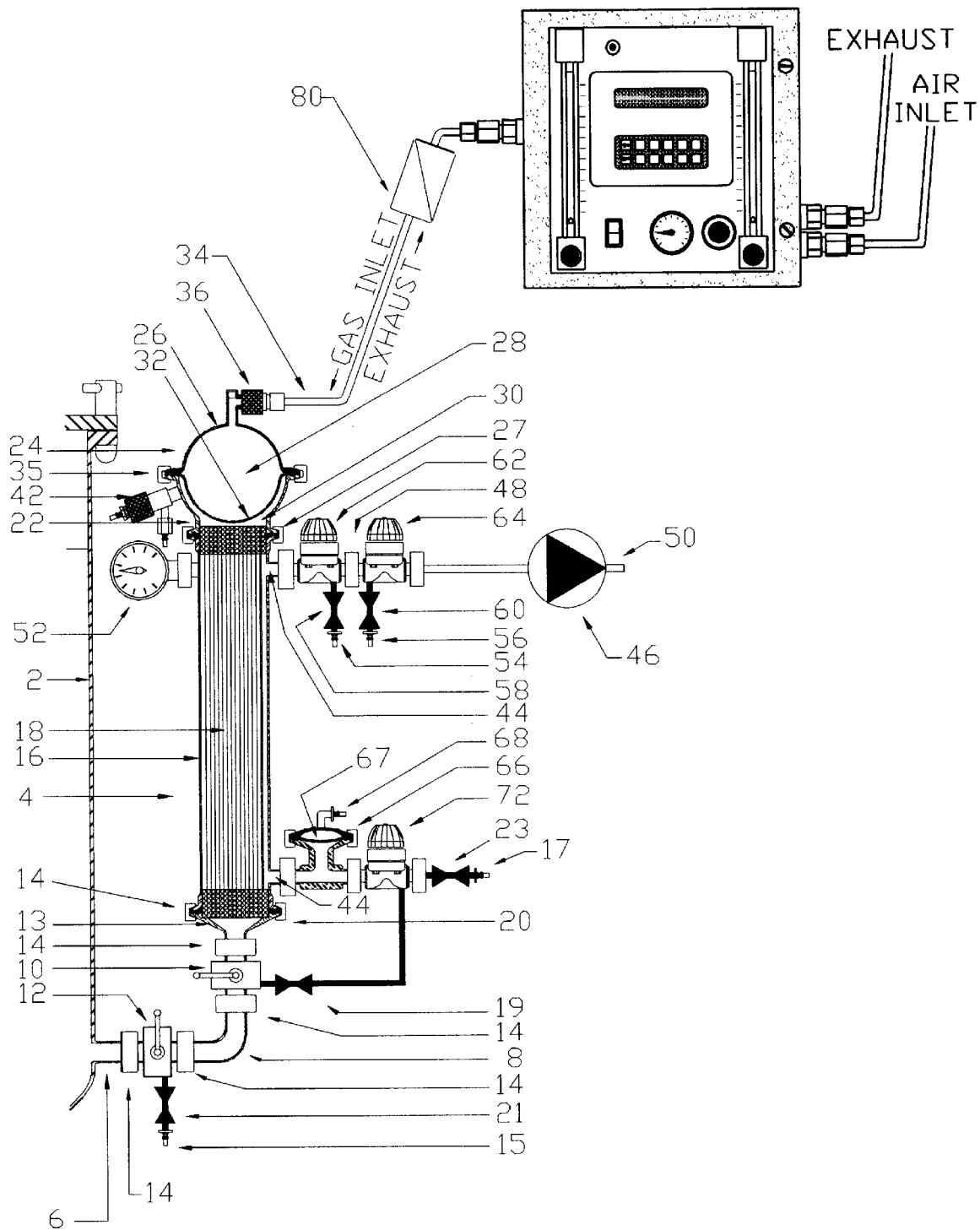
FIG. 1 shows a first embodiment of an alternating tangential flow filtration system according to the invention showing a harvest port at a top side part of a filter compartment.

Referring to FIG. 1 there is shown a fluid filtration system according to the invention. A process vessel 2 is connected via a fluid connector to a filter containing compartment 4. The vessel 2 may be any suitable container for a fluid to be filtered. For example, it may be a bioreactor, a fermentor or any other vessel, nonexclusively including vats, barrels, tanks, bottles, flasks, containers, and the like which can contain liquids. The vessel may be composed of any suitable material such as plastic, metal such as stainless steel, glass, or the like. The fluid connector serves to direct a fluid from the storage vessel into an entrance end of a filter containing compartment.

The fluid connector may comprise a vessel port 6, suitable for flowing fluid into and out of the vessel, attached to joint 8 which is in turn is connected to the entrance end of the filter containing compartment 4. Suitable ports nonexclusively include any sanitary, leak-proof fittings known in the art such as a compression, standard Ingold or a sanitary type fitting. Suitable joints nonexclusively include pipes, tubes, hoses, hollow joint assemblies, and the like. For a penetration into a lower side of a vessel, the most preferred fluid connecting means is an L-shaped pipe as shown. The joint may vary from one system to another, based on the configuration and requirements of the vessel and process. Joint 8 is connected both to the vessel port 6 and the entrance end of the filter containing compartment 4 via appropriate valves 10 and 12. The joint 8 may be attached to the valves 10 and 12 by suitable clamps 14, such as a triclamp sanitary fitting or the like. This does not preclude the use of other appropriate connections. The filter containing compartment 4 comprises a filter housing 16 which holds a replaceable filter element cartridge 18. The connection between valve 10 and housing 16 may be direct or indirect should there be a mismatch between the corresponding fittings. In one example, should the housing 16 contain a 2.5 inch sanitary end and valve 10 contain a ½ sanitary end, a 2.5 by ½ inch sanitary adapter 13 may be used to join the two ends.

The fluid connector also preferably has at least one, and preferably two secondary openings suitable for introducing or expelling liquids or gases into and out of the system for cleaning or sterilizing the connector. The flow into or out of such openings may be further regulated with secondary valves 19, 21 or 23. In the most preferred embodiment the fluid connector has at least one steam inlet line 17 and at least one condensate outlet 15. These steam inlet and condensate outlet lines are preferably used for sterilization of the connector 8. In order to sterilize the joint, valves 10, 12 and 72 are closed to the vessel port 6, filter housing 16 and filtrate compartment 7 (FIGS. 2A–2C), and steam is injected into inlet 17 via valves 19 and 23. Condensate is removed from outlet 15 via valve 21. In another configuration, inlet 17 may be connected directly to valve 19 to achieve the same sterilization results of the joint between valves 10 and 12. Upon completion of the sterilization, valves 19 and 21 are closed, valves 10 and 12 are opened, alternating tangential flow resumed and the filtration process continued.

The filter containing compartment 4 preferably has an entrance end 20 and an exit end 22. The entrance end is attached to the joint assembly with a clamp 14, if entrance end 20 is attached directly to valve 10. Such connection may require a second clamp in addition to 14 if the connection is indirectly through an adapter 13. Exit end 22 is connected to a diaphragm pump 24 by means of clamp 27. Suitable materials for the housing of the filter containing compartment nonexclusively include plastic, metal, such as stainless steel, glass, and the like. Most preferably, the housing comprises stainless steel. Suitable removable filter elements nonexclusively include hollow fiber filters, screen filters, and the like. Most preferably, the removable filter element is a hollow fiber filter or filters consisting of a screen mash. According to the invention, the filter element can be removed from the fluid filtration system before, during, or after the filtration process. Suitable hollow fiber filtration membranes or screen filters are commonly available from various vendors.

The diaphragm pump 24 is used to move the fluid from the vessel 2 through the filter 18 in the filter containing compartment 4 into the pump 24 and then reversing the fluid flow from pump 24 back through the filter to vessel 2. In this way, an alternating tangential flow of fluid is generated through filter 18. In the case where filter 18 is a hollow fiber cartridge, both ends, the entrance end 20 and the exit end 22, of 18 are sealed against the housing wall to prevent mixing of the retantate side 3, and the filtered side 7 of the filter. The retantate side of the fiber being the lumen side of the hollow fiber and the filtrate side being the shell side of the hollow fiber. Such a leak proof seal can be formed by a number of methods, including O rings, gaskets or any other means that form an impenetrable barrier between the circumference at each end of the filter and the inner wall of the housing. Alternating flow of retantate between pump 24 and vessel 2 is through the lumen side of the filter or compartment 3.

The diaphragm pump 24 preferably comprises a pump housing 26 separated into first and second interior chambers 28 and 30 by an internal diaphragm 32. The diaphragm is flexible, and is preferably fixed inside the housing via a leak proof, sanitary fitting 35. The diaphragm may be uniform in thickness, or may vary somewhat in thickness or shape, as the process may require. In one example, a thicker region is formed at the center of the diaphragm. The thicker region may face towards compartment 28. During an exhaust cycle or during sterilization, when the diaphragm is forced into exhaust/air inlet port 36, such a thicker region will offer the diaphragm added structural support. The diaphragm pump has an entrance end through which fluid flows from the exit end 22 of the filter containing compartment 4 to the second, interior chamber 30 of pump 24. Pump chamber 28 isolates and contains the mechanism for driving the diaphragm within pump 24 without contaminating the fluid content in the adjacent chamber 30. The pump is pneumatically actuated by alternately feeding a gas, such as air through a reversible inlet/exhaust line 34. The inlet/exhaust line 34 is attached to pump 24 via a connector 36 such that when the gas is passed through the line 34, it is injected into the first chamber 28 of the pump and fills the first chamber 28 with the gas expanding the chamber and flushing any fluid in the second chamber 30 in a direction toward and through the filter 18. Typically, but not exclusively, a controlled addition of compressed air into through 34 may be used to expand chamber 28, inversely, reducing the volume in the adjacent pump chamber 30, driving the content from chamber 30 to vessel 2. When the gas is drawn back through line 34, such as by a vacuum source, not shown, in the indicated exhaust direction, the diaphragm 32 is drawn towards the gas inlet 36. Chamber 28 decreases in volume, allowing flow from vessel 2 through the filter module 18 and into expanding chamber 30. Bidirectional flow control of air through line 34 may be regulated by microprocessor control of a suitable 3-way or 4-way solenoid valve, not shown. This action repeats drawing fluid back and forth from the vessel 2, through the filter, and chamber 30 causing an alternating flow tangentially through the filter 18. Chamber 28, which is connected to a gas inlet/exhaust line 34 may contain a hydrophobic filter 80 for allowing a gas such as air to freely flow through line 34 while preventing liquid flow therethrough. The fluid filtration system preferably also comprises a controller for controlling the movement of the diaphragm within the pump housing. FIG. 1 shows an alternating tangential flow controller. The controller may comprise a pressure measuring device such as a pressure transducer which serves to monitor and or regulate the pressure in chamber 28 and 30 relative to the process vessel 2. It may be used to trigger a reversal of gas flow via line 34 into and out of chamber 28 and hence fluid flow into and out of chamber 30 by triggering the switching and controlling the expansion and contraction of the diaphragm within the pump housing. Other means of switching the movement of the diaphragm, such as the use of proximity switches, are also within the contemplation of the invention. It is noted that pump chambers 28 and 30 need not be of the same size nor do they have to be spherical as shown. They may be adjusted to the requirement of the process by the alternating tangential flow (ATF) controller as shown. As a result, fluid flow back and forth through the filter is controlled. For example, when working with animal cells, cells may be damaged if chamber 28 expands to the point where the diaphragm 32 is forced against the inner pump wall of chamber 30. To minimize or prevent the entrapment of cells between the pump wall and diaphragm, the chamber 30 wall may have a somewhat larger radius than the radius of the chamber 28 wall. With the diaphragm 32 having the same radius as chamber 28, expansion of chamber 28 need not drive the diaphragm to the chamber 30 wall, and sufficient space is maintained between the diaphragm and the pump wall. Controlled expansion of chamber 28, the selection of diaphragm materials and, if desired, the use of sensors may accurately control the position of the diaphragm in the pump.

It is also preferred that the diaphragm pump contains at least one secondary opening which is connectable to at least one sampler valve 42. Valve 42 may be used for a variety of purposes including sampling the quality of the fluid in chamber 28, injecting or expelling any liquid or gas into and out of chamber 30, injecting sterilizing steam into the system or removing resulting steam condensate from the system. For example, the sampler valve may also be suitable for injecting air into the system to expel liquid from the system into the process vessel prior to detachment of the filter system from the process vessel; conversely, it may be used to purge air from the system prior to initiating alternating tangential flow. The sampler may be used for other desired purposes.

The filter containing compartment 4 also preferably has at least one opening 44 which is suitable as a fluid harvest port. The fluid harvest port 44 is suitable for removing filtered fluid from the filter compartment 4. In the most preferred embodiment, a filtrate pump 46 is connected to the harvest line 50. The filtrate pump 46 is suitable as a means for controlling the removal of filtered fluid from the system and to serve as a check valve to regulate the unrestricted flow of filtrate from compartment 7. Pressure in the housing 16 may be monitored by a pressure valve or transducer 52. The harvest line 50 may be provided with suitable valves to allow making or breaking the harvest line, as needed, during filter replacement or for any other reason. In one example, line 50 contains valves 62 and 64 joined to each other in series with clamp 48. The same valves are also fitted with a steam inlet and/or condensation removal lines 54 and 56 for cleaning and/or sterilizing the harvest line 50 along joint 48. With valves 62 and 64 closed, steam flow through lines 54 and 56 and through the segment between valves 62 and 64, may be controlled with valves 58 and 60. Therefore, line 50 may be severed and recombined in a sterile manner at clamp 48. As will be demonstrated the harvest line joint assembly may be used in the described configuration or in some other configuration, as needed by the process or different steam sterilization regiments.

The filter containing compartment 4 preferably has at least one secondary opening suitable for dampening the pressure in the overall system. A pressure dampener 66 may be connected to a suitable port 44 through filter housing 16. The pressure dampener serves to dampen and control the pressure fluctuations within filter housing 16 that result in response to the changing pressures in chamber 30 of pump 24 during the alternating flow cycle. The pressure dampener may comprise an elastic element 67 such that during pressurization cycle when compartment 30 is at maximum pressure and the pressure differential across the filter membrane is also at its greatest there is greater flow from the retantate side 3 into compartment 7 and into the 66. Without a pressure dampener, the relatively rigid confines of housing 16 will allow only negligible, inelastic, inflow of filtrate into compartment 7 until the pressure across the membrane equilibrates; however, with an elastic membrane or diaphragm 67 in the pressure dampener, greater flow occurs across the membrane because of the elastic response of diaphragm to the increased pressure. The efflux of filtrate will continue until the pressure equilibrates between compartments 3 and 7 across the filter membrane. The volume taken up by the pressure dampener 66 will depend on various factors, including, configuration of the pressure dampener, elasticity of membrane 67, the pressure differential across membrane 67 and the pressure in compartment 7. During an exhaust cycle of pump 24, when chamber 28 and 30 are at lower pressure relative to chamber 7, flow from the pressure dampener is reversed. Flow is from chamber 7 across the filter membrane into chamber 3. With an inelastic housing 16 there will be negligible back flow from compartment 7 to compartment 3. However, the excess volume taken-up by the pressure dampener at the higher pressure cycle may now pulse back into compartment 3, generating a back-flush. Such a back-flush during each filtering cycle results in further clearing of particulates or gelatin build-up on the inner wall of the filter 18. The process can contribute significantly to the maintenance of filtration longevity.

Furthermore, such a pressure dampener can be configured to comprise a simple elastomer that responds passively to the changing pressures in housing 16 or one may also use a pressure dampener which responds actively to the changing pressures. One example of the latter is a system which controls the gradual influx of filtrate into the pressure dampener over several cycles of the pump, than rapidly expels excess medium accumulated in the dampener for a more powerful back-flush. The active control of membrane 67 may be pneumatically with air through port 68 or by some other active means. The type of pressure dampener used may be optimized by those skilled in the art depending on the end use.

The filter containing housing 16, pump 24, diaphragm 32, valves, filters and other constituents of the system may be constructed of any number of material, preferably such materials that withstand the temperature and pressure conditions of sterilization in an autoclave or steam in place regiment. Depending on use, however, the filtration system may also be constructed of materials that may be sterilized by gas or radiation; furthermore, where sterility is not required, any number of materials may be used. A preferred material is stainless steel. One of the primary disadvantages of Stainless steel is the inability to view the content inside housing 16. This shortcoming can be alleviated with a sight port or window in the housing strategically placed to view the content inside.

Figure 2:
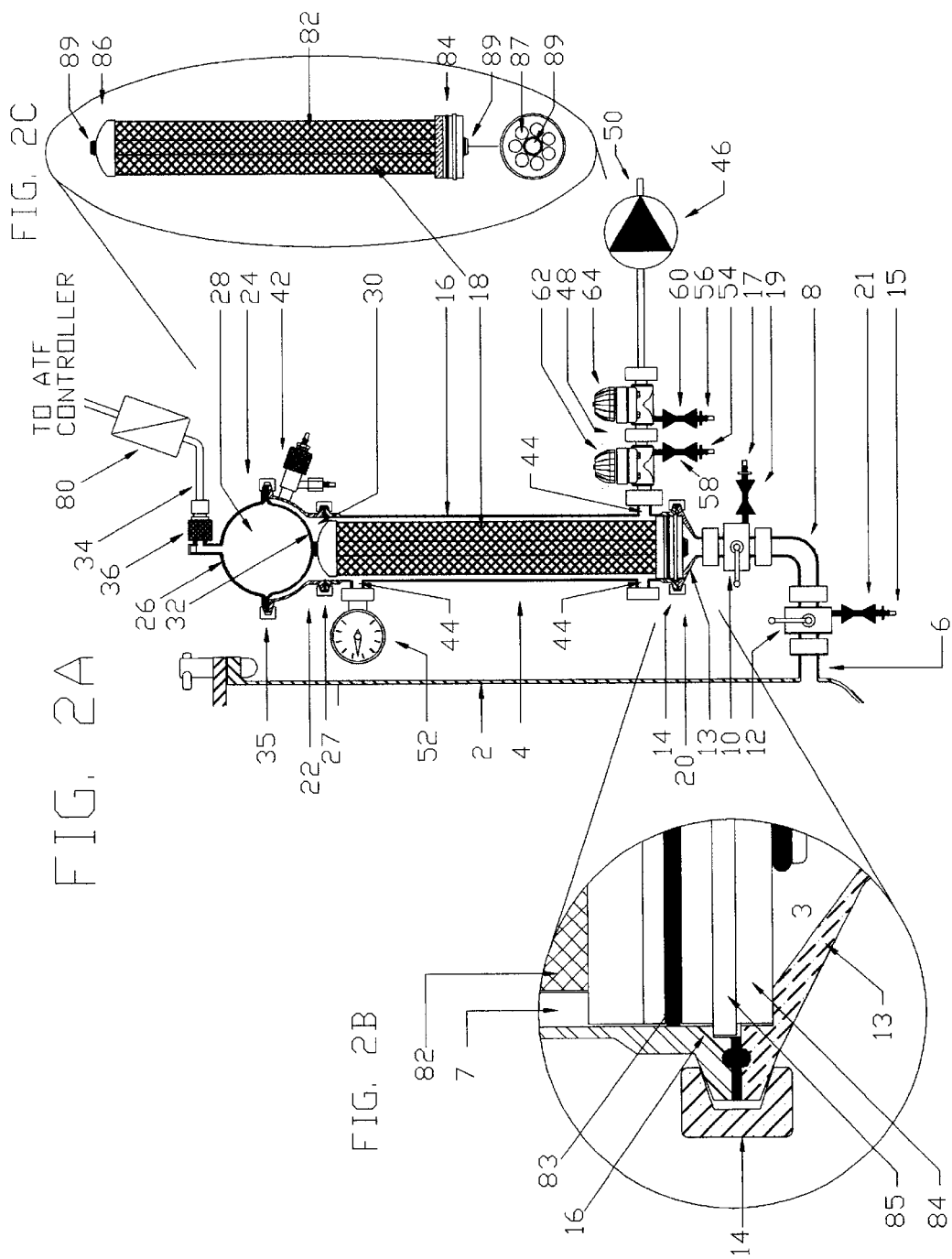
FIGS. 2A–2C show another embodiment of an alternating tangential flow filtration system according to the invention showing a harvest port at a bottom side part of a filter compartment.

While a single embodiment of the invention has been disclosed in detail, many other variations are contemplated. FIGS. 2A–2C show another embodiment of the invention where a screen mesh filter module 18 is used instead of the hollow fiber filter module described above. In the example shown, such a screen module 18 contains a base 84, a stop 85, a top 86 and a post 89 to fix the distance between the base and the top. A tubular screen mesh filter 82 contains O rings fixed to its ends. Screen mesh filter may be comprised of a nylon, stainless steel or polyester screen fabric which serves to filter the fluid passing within compartment 4. The screen spacing may be easily determined by those skilled in the art depending on the use under consideration. In a like manner to the use of hollow fiber filters, fluid to be filtered flows between the process vessel 2 and the diaphragm pump. However, filtered fluid is removed from the filter containing housing perpendicularly to the filter out harvest line 50. In a preferred embodiment, the screen has a open spacing ranging from about 5 $\mu$m to about 200 $\mu$m, or more preferably from about 20 $\mu$m to about 75 $\mu$m. The O rings are inserted into O ring grooves in the base and top of the screen module and the O rings are retained in the O ring grooves with retaining rings; thus, the periphery of the screen module 18 is enclosed by the screen. The module 18 can be inserted, with the top first, into filter housing 16 either from end 22 that registers with diaphragm pump 24 or from the end 20 that registers with adapter 13. Referring to the exploded view in FIG. 2B, an O ring 83 in base 84 seals the base against the inner wall of housing 16. With top 86 fully closed, the only entry into or from the screen module 18 is through channels 87 in the base. By Insertion of module into housing 16 through end 20 allows, the retantate compartment 3 constitutes the inside of module 18 and the path to vessel 2 through connector 8. The filtrate side 7 constitutes the compartment outside the module. In such configuration, collection of filtered harvest can take place from any port 44 or the sampler 42, while larger unfiltered particles are retained in compartment 3 and process vessel 2.

The system shown in FIGS. 2A–2C, or in some other possible configuration may find applications in perfusion or medium exchange of anchorage dependent cells using microcarriers, or any other application requiring fractionation, harvesting or concentration of particles by size. Particle larger than the screen opening will be retained. The alternating flow generated by pump 24 facilitates the separation process. For example, in the configuration shown in FIGS. 2A–2C, microcarrier free medium can be removed from the system through filtrate line 50. The microcarriers being larger than the opening in the screen are retained in the system. Any microcarriers that adhere to the screen during filtration or during the exhaust cycle of pump 24 will be dislodged from the screen and returned to the vessel during the air inlet cycle of the pump. This process may be performed with housing 16 and pump compartment 30 full with liquid or with minimum liquid, consisting of only the volume displaced by the pump. Other variations of the process are possible, including varying pump exhaust and air inlet rate and cycle time, position of screen module, harvest process or other such variations as needed to suit the process.

Figure 3:
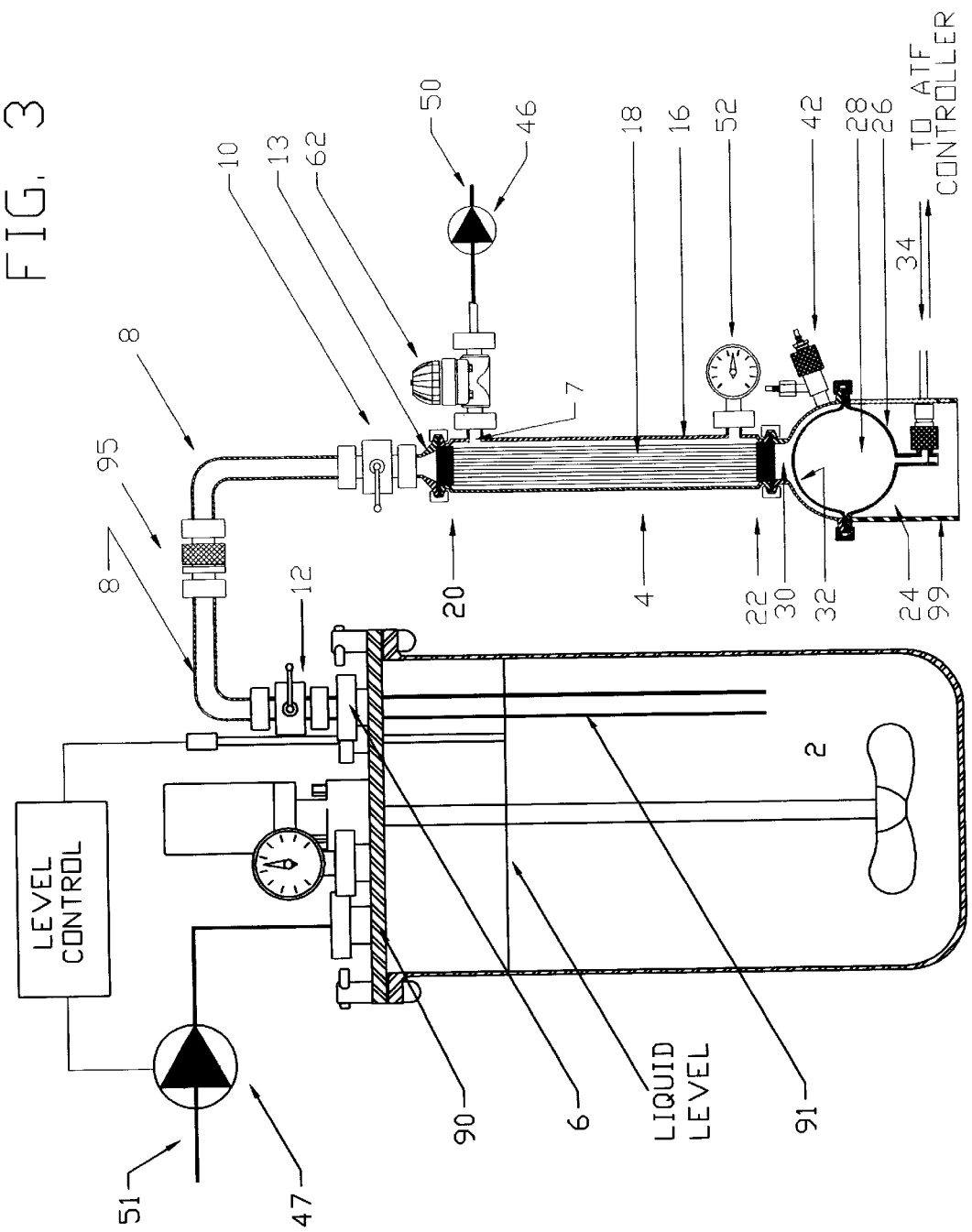
FIG. 3 shows another embodiment of an alternating tangential flow filtration system according to the invention showing process fluid from a vessel entering a filter housing through an opening at its top and a pump at a bottom of the filter housing.

FIG. 3 shows yet another variation of the invention. In some application it may be desirable to penetrate the process vessel 2 through an opening other than the side opening described above. Shown is top penetrating port 6 through a head plate 90 of process vessel 2. While the relationship between system components including pump 24, the filter compartment 4 and the connector 8 remain the same, the entire system is inverted. The inlet side 20 and the exit side 22 of the filter housing 16 retain their relationship to the pump 24 and to connector 8. Note, however, that to generate alternating tangential a dip tube 91 is used to connect the filtration system to the liquid in the process vessel. Connection 8 need not be rigid and connection 95 may facilitate making and breaking connection 8. A stand 99 or some other support positions the filtration system in the desired orientation. Filtered harvest is collected from compartment 7 through line 50. Liquid removed may be restored by a level control mechanism that activated an addition pump 47 to pump liquid into the vessel through line 51.

Other variation of the invention are also possible. For example, multiple filter containing compartments, with corresponding secondary opening may be connected to a single pump. When multiple filter containing compartments are used, they may be disposed in series formation or in parallel formation relative to each other. Alternatively, when multiple filter containing compartments are disposed in parallel formation, each filter containing compartment may be connected to a separate diaphragm pump. In another configuration, multiple filters may be contained in a single housing, not unlike the described system where such housing will be attached at one end to a diaphragm pump 24 and at the other end to a joint assembly for appropriate connection to a process vessel.

The diaphragm pump 24 and filter containing compartment 4 may be disposed horizontally or vertically relative to each other. When disposed vertically, the diaphragm pump may be disposed vertically above or vertically below the filter containing compartment. Most preferably, the diaphragm pump is disposed vertically above the filter containing compartment. While multiple diaphragm pumps may be used simultaneously in the practice of the present invention, one diaphragm pump is most preferably used.

In use, the diaphragm pump 24 serves to generate an alternating tangential flow through the filter 18. The pump 24 generates a pulsating, reversible, flow of liquid such as a culture suspension, back and forth, between process vessel 2 and diaphragm pump 24. Depending on the process requirements, flow between vessel 2 and pump 24 may have to be generated somewhat differently. In one case, where vessel 2 is a pressure vessel and is maintained sufficiently above atmospheric, the flow from pump chamber 30 through the filter 18 to process vessel 2 is generated by pressurizing chamber 28 relative to the pressure in vessel. Expansion of chamber 28 by addition of air from line 34 expels the liquid from chamber 30 towards vessel 2, generating a tangential flow in one direction. Inversely, when using a pressure rated vessel 2, and maintaining the vessel somewhat pressurized, a controlled exhaust from chamber 28 causes the pressure in 28 to decrease relative to the pressure in vessel 2. The flow path is reversed, from vessel 2 back to chamber 30, generating tangential flow in the opposite direction. Flow from pump 24 to vessel 2 and return from vessel 2 to pump 24 completes one cycle. In an embodiment where vessel 2 is not pressurized, e.g., glass vessel, there will be no pressure driving force to move the liquid in vessel 2 to chamber 30. In this case, flow from the vessel 2 to chamber 30 is achieved by connecting a vacuum to chamber 28. Pressurizing chamber 28 relative to the vessel 2 will produce return flow from chamber 30 to vessel 2. The cycle or pulse rate and the flow rate between pump and vessel will depend primarily on the configuration of the pump and pressure differential between pump and vessel and the control mechanism used to regulate the cycle. In addition, the flow rate through the filter will be a function of variables such as hollow fiber tube inside diameter, number and length of fibers, the properties of the medium flowing through the filter, filtration rate, configuration of the system, etc.

While the rate of expansion and contraction of chamber 28 is a function of the air flow rate in out of that compartment, the actual duration of each portion of that cycle can be set by a variety of mechanisms. For example, one way to set the duration of each part of the cycle is with a timing mechanism. Pressurization time is set to a specific duration. At the end of that time interval, a solenoid valve switches line 34 from pressurization to exhaust. Similarly, at the end of the preset exhaust time, the valve will return to the original setting to repeat the cycle. Using timing mechanism to control each part of the cycle, however, while simple, may not provide optimum results. Preferably, the set time intervals should coincide with the time required to achieve the maximum or minimum volume of chamber 28, or:

$$t_p - t_{max} = 0$$

$$t_e - t_{min} = 0$$

where:

$t_p$=pressurization time $t_e$=exhaust time $t_{max}$=time required to reach chamber 28 maximum volume, pressurization cycle $t_{min}$=time required to reach chamber 28 minimum volume, exhaust cycle.

Setting the times, $t_p$ and $t_e$, to coincide, precisely, with the maximums and minimums of chamber 28 volume, $t_{max}$ and $t_{min}$, during pressurization and exhaust, respectively, is somewhat difficult. While set times, $t_p$ and $t_e$, can be accurately controlled, the pressure in the process vessel, air inlet or exhaust are more difficult to control; a change in any one of these parameters can offset $t_{max}$ and $t_{min}$. Any time $t_p > t_{max}$ and $t_e > t_{min}$ interrupts the continuous flow between chamber 30 and vessel 2 by the amount $t_p - t_{max}$ and $t_e - t_{min}$. In the case of hollow fiber filtration, such interruption in flow causes the system to revert from the efficient tangential flow filtration to the less efficient dead-end filtration, reducing the life of the filter. Any time $t_p<t_{max}$ and $t_e<t_{min}$ less than maximum capacity of the pump is being used. Air flow rate into or from compartment 28 may be controlled by a variety of methods including manual flow control devices or automated mass flow regulators.

The system of the present invention may be used for filtering, concentrating, clarifying or otherwise conditioning a fluid or process medium when used with the appropriate filter element. The system may also be used as a sampler, suitable for extracting filtered stream from a process vessel while allowing continuous monitoring and analysis of the process. The back and fourth flow of medium between vessel and filter allows continuous equilibration of the process medium between these two compartments. The filtered stream is therefore representative of the content in the vessel.

The system of the present invention is most preferably used for filtering fluids, most preferably biological fluids. Nonexclusive examples of biological fluids include microcarrier based cultures, blood, and other fluids containing animal, microbial or plant cells. Although a preferred embodiment of the present invention is disclosed with regard to filtering a biological fluid, it is understood that the present invention can be used for filtering other liquids.

Furthermore with the appropriate connection to the likes of vessel 2 or some other device, one may establish an automated self cleaning system.

Instead of process fluid, cleaning solutions may be added to vessel 2 or a similar appropriate device. A single or multiple alternating filtration systems may be attached to such device or vessel. Maintaining active alternating tangential flow process may be used to clean the internal components of the system or the filter inside. Various such self cleaning regiments may be established.

In one preferred embodiment, a storage vessel is provided with a biological fluid to be filtered. Compressed air is added into pump 24 to expand the first interior chamber 28 of pump, inversely reducing the volume in the second interior chamber 30. This forces the contents of the second interior chamber 30 into the filter containing compartment 4, through the filter element 18, and to the storage vessel 2. This flow of fluid from the diaphragm pump 24 to storage vessel 2 generates a tangential flow in one direction. Inversely, the flow of fluid may be reversed by decreasing the volume in the first interior chamber 28 of the diaphragm pump 24, thus generating tangential flow in the opposite direction. The flow of fluid from the second interior chamber 30 to the storage vessel 2, and return from the storage vessel to the second interior chamber completes one cycle of the filtration system and alternating tangential flow.

The low shear nature of the pump, the ability to confine the process, and the other described properties can facilitate its is as a medical device. Some areas where this may be applicable is in dialysis or organ perfusion. For example, in dialysis, two units, containing the appropriate filters may be used. The use of two units will allow the maintenance of a constant volume that will flow between patient and the dialysis system; i.e., as blood flows from patient to one of the modules, a concomitant flow is generated in the opposite direction from the second module to the patient. The efficiency of the process, in the general configuration described, can facilitate the production of a more efficient, more compact dialysis unit that will be more beneficial to the patient.

When using materials that are not as shear sensitive as are living cells or certain biological materials, one may use the filtering system at high pressures and flow rates. In combination with narrow bore filter, high sheer may be generated.

An important attribute of the invention is the closed nature of the system. The enclosed nature of the system also allows filtration applications with hazardous materials (i.e., corrosive, flammable, organic, etc.), provided the appropriate filters are used that are compatible with the process. This may include the use of filters made from metals, ceramics or other material. Similarly, the diaphragm and other components of the system may be made from any number of materials that will allow compatibility with the requirement of the process. The process vessel 2, the filter compartment 4, the diaphragm pump 24 and all other components are connected in such a manner as to totally confine the process. The use of pressure rated components, such as stainless steel for the vessel 2, filter containing compartment 4, diaphragm pump 24 and other parts of the system, allows steam sterilization of the entire system. One may therefore steam sterilize the perfusion system prior to use or during a production run, if a filter needs to be replaced. A significant advantage which this invention provides is the ability to sterilize the entire system or any parts of the system by the controlled opening and closing of the appropriate valves such as 10, 12, 19, 21, 58, 60, 72 and sampler 42 together with the injection of cleaning fluid or steam and collection of waste cleaning fluid or stream condensate. The system may be sterilized at any time by injecting steam into any opening in the system and then expelling the resulting condensate from any opening in the system. Accordingly, each component of the system may be sterilized separately while the system is still intact. This can be done by closing various connectors to isolate the steam in a particular system component. With the capacity for steam sterilization, the filter 18 may be easily replaced by flushing the fluid out of the pump 24 and housing 16 into vessel 2, closing valve 12, opening clamp 14 and/or 27, removing the consumed filter 18, cleaning the pump, filter housing 16 and associated lines, ports and opening, replacing the filter, closing clamps 14 and 27 followed by sterilization. Valve 12 is then opened. The pumping process may then be restarted. At any desired time, the filtered fluid may be harvested by opening valves 62 and 64 and collecting filtered fluid by pre-sterilized line 50 via pump 46.

It has been found that the cell concentration achieved in the perfusion according to the invention is from about 1 to about 20 times that achieved in a batch process. Removing the need to drive cells through a pump head removes a large source of shear from the system and requires only a single connection to the vessel. Conventional pumps, including peristaltic, impeller driven and to a lesser degree diaphragm types, generate flow by adding energy to the liquid in the form localized pressure gradients. The resulting high turbulent flow is highly destructive to cells; in addition, such in-line pumps typically require two connections to the process vessel. On the other hand, pressurizing or depressurizing chamber 28 relative to vessel 2, generates a highly laminar, low shear flow. Since air flow may be used as the driving force for moving the culture medium through the filter, one can generate very rapid tangential flow rates. Unlike other pumps, the driving energy is added to the surface of the liquid over a large area and not localized in the liquid; therefor, scale up and high flow rates are achieved with minimum addition of shearing energy to the culture.

The dynamics of the inventive system can extend the operating life of a perfusion run since pulsating flow between vessel 2 and chamber 30 greatly inhibit the attachment of aggregates to the hollow fiber lumen or to the filter membrane. For example, as culture medium flows from vessel 2 to pump 34, aggregates that are larger than the inside diameter of the hollow fibers will be retained by the hollow fiber array; i.e., the hollow fibers will act as a filter, however, by repeated and rapid reversal of flow direction, the deposited aggregates are quickly removed and swept back to the vessel. In contrast, the longer the flow is maintained, continuously in one direction, the greater the probability that particles will become permanently lodged at the inlet end of the hollow fibers. The pulsating flow, back and forth between vessel and pump inhibits both the attachment and growth of an obstruction at either end of the filter.

Additionally, blockage of the filter is inhibited by a changing pressure differential generated across the filter wall. The use of a pressure dampener facilitates this process. The changing pressure within the filter lumen as a function of pump cycle results in a differential pressure that can be either positive or negative across the filter wall. Such momentary reversal in filtrate flow, back into the lumen, can inhibit gelatin formation and clogging of the filtration membrane.

While the present invention has been particularly shown and described with reference to preferred embodiments, it will be readily appreciated by those of ordinary skill in the art that various changes and modifications may be made without departing from the spirit and scope of the invention. It is intended that the claims be to interpreted to cover the disclosed embodiment, those alternatives which have been discussed above and all equivalents thereto.

What is claimed is:

1. A fluid filtration system comprising:
   a) at least one fluid storage vessel;
   b) at least one filter containing compartment;
   c) a fluid connector attached to the storage vessel and to an entrance end of the filter containing compartment, which connector is capable of directing a fluid from the storage vessel into the entrance end of the filter containing compartment;
   d) at least one diaphragm pump connected at a retentate exit end of the filter containing compartment; which diaphragm pump is capable of alternately receiving fluid from the retentate exit end of the filter containing compartment and arranged for then expelling the fluid back into the retentate exit end of the filter containing compartment; and
   e) at least one fluid harvest port connected to the filter containing compartment for removing filtered fluid from the filter containing compartment.

2. The fluid filtration system of claim 1 wherein the fluid connecting means comprises a pipe connected between the fluid storage vessel and the filter containing compartment.

3. The fluid filtration system of claim 1 which further comprises at least one filtrate pump connected to the fluid harvest port.

4. The fluid filtration system of claim 1 which further comprises at least one pressure dampener connected to the filter containing compartment.

5. The fluid filtration system of claim 1 which further comprises at least one steam inlet line connected to the fluid connecting means.

6. The fluid filtration system of claim 5 which further comprises at least one steam outlet line connected to the fluid connector.

7. The fluid filtration system of claim 1 which further comprises at least one pressurized gas inlet connected to the diaphragm pump.

8. The fluid filtration system of claim 7 which further comprises at least one exhaust outlet connected to the diaphragm pump.

9. The fluid filtration system of claim 1 which further comprises at least one fluid sampler valve connected to the diaphragm pump.

10. The fluid filtration system of claim 1 which further comprises a pressure gauge connected to the diaphragm pump.

11. The fluid filtration system of claim 1 wherein the fluid storage vessel is a bioreactor.

12. The fluid filtration system of claim 1 wherein the filter containing compartment comprises a removable filter element.

13. The fluid filtration system of claim 12 wherein the removable filter element comprises hollow fibers.

14. The fluid filtration system of claim 12 wherein the removable filter element comprises a screen filter.

15. The fluid filtration system of claim 1 wherein the diaphragm pump and the filter containing compartment are disposed vertically relative to each other, with the diaphragm pump above or below the filter containing compartment.

16. The fluid filtration system of claim 1 wherein the diaphragm pump and the filter containing compartment are disposed horizontally to each other.

17. The fluid filtration system of claim 1 comprising a plurality of filter containing compartments disposed in series relative to each other.

18. The fluid filtration system of claim 1 comprising a plurality of filters in a filter containing compartment.

19. The fluid filtration system of claim 18 wherein each filter containing compartment is attached to a diaphragm pump.

20. The fluid filtration system of claim 1 comprising a plurality of filter containing compartments disposed in parallel relative to each other.

21. The fluid filtration system of claim 1 wherein the diaphragm pump comprises a pump housing having two interior chambers separated by an internal diaphragm; wherein the interior chamber positioned closest to the exit end of the filter containing compartment has a larger radius than a radius of the interior chamber positioned further away from the exit end of the filter containing compartment.

22. A process for filtering a fluid comprising:
   a) providing a fluid filtration system comprising at least one fluid storage vessel;
      at least one filter containing compartment; a fluid connector attached to the storage vessel and to an entrance end of the filter containing compartment, which connector is capable of directing a fluid from the storage vessel into the entrance end of the filter containing compartment;
      at least one diaphragm pump connected at an exit end of the filter containing compartment; which diaphragm pump is capable of alternately receiving fluid from the exit end of the filter containing compartment and then expelling the fluid back into the exit end of the filter containing compartment; and at least one fluid harvest port connected to the filter containing compartment for removing filtered fluid from the filter containing compartment;
   b) filtering a fluid by causing the fluid to flow from the storage vessel through the filter containing compartment and then to the diaphragm pump;
   c) re-filtering the fluid by causing at least a portion of the fluid to flow from the diaphragm pump through the filter containing compartment and then the storage vessel;
   d) optionally repeating steps b and c; and
   e) removing the filtered fluid from the filtration system.

23. The process of claim 22 wherein the diaphragm pump creates an alternating tangential flow of the fluid between the storage vessel and the diaphragm pump.

24. The process of claim 22 wherein the fluid comprises a culture growing medium.

25. The process of claim 22 further comprising the step of adding fresh fluid to the filtered fluid.

26. A process for sterilizing a fluid filtration system comprising:
   a) providing a fluid filtration system comprising at least one fluid storage vessel;
      at least one filter containing compartment; a fluid connector attached to the storage vessel and to an entrance end of the filter containing compartment, which connector is capable of directing a fluid from the storage vessel into the entrance end of the filter containing compartment;
      at least one diaphragm pump connected at an exit end of the filter containing compartment; which diaphragm pump is capable of alternately receiving fluid from the exit end of the filter containing compartment and then expelling the fluid back into the exit end of the filter containing compartment; and at least one fluid harvest port connected to the filter containing compartment for removing filtered fluid from the filter containing compartment;
   b) injecting steam into at least a portion of the fluid filtration system via at least one steam inlet; and
   c) removing the steam from the fluid filtration system via at least one steam outlet.

27. A fluid filtration system comprising:
   a) at least one fluid storage vessel;
   b) at least one filter containing compartment;
   c) a fluid connector attached at one end thereof to the storage vessel by a valve, and attached at another end thereof to an entrance end of the filter containing compartment by a valve, which connector is capable of directing a fluid from the storage vessel into the entrance end of the filter containing compartment; said fluid connector having a steam injection port and a condensate outlet;
   d) at least one diaphragm pump connected at an exit end of the filter containing compartment; which diaphragm pump is capable of alternately receiving fluid from the exit end of the filter containing compartment and expelling the fluid back into the exit end of the filter containing compartment; said diaphragm pump having a pump housing comprising a first and a second chamber separated by a diaphragm; the first chamber of the diaphragm pump being connected to a gas port capable of alternately injecting a gas into and out of the first chamber; the second chamber being in fluid flow cooperation with the exit end of the filter containing compartment; a controller for controlling the movement of the diaphragm within the pump housing; a fluid sampling port attached through a wall of the second chamber;
   e) at least one fluid harvest port connected to the filter containing compartment for removing filtered fluid from the filter containing compartment, said harvest port being connected via a fluid flow line to a fluid pump; first and second fluid control valves attached in series between the harvest port and the fluid pump; a steam injection port and a condensate outlet attached to the fluid flow line between the steam injection port and a condensate outlet;
   f) a pressure dampener attached through a wall of the filter containing compartment;
   g) wherein the filter which comprises a plurality of bundled hollow fibers whose axes extend longitudinally from the entrance end to the exit end of the filter containing compartment.

28. A fluid filtration system comprising:
   at least one filter containing compartment;
   a fluid connector attached to an entrance end of the filter containing compartment, which connector is capable of directing a fluid from a vessel into the entrance end of the filter containing compartment;
   at least one diaphragm pump connected at a retentate exit end of the filter containing compartment; which diaphragm pump is capable of alternately receiving fluid from the retentate exit end of the filter containing compartment and arranged for then expelling the fluid back into the retentate exit end of the filter containing compartment; and
   at least one fluid harvest port connected to the filter containing compartment for removing filtered fluid from the filter containing compartment.

29. A process for filtering a fluid comprising:
   a) providing a fluid filtration system comprising at least one filter containing compartment; a fluid connector attached to an entrance end of the filter containing compartment, which connector is capable of directing a fluid from a vessel into the entrance end of the filter containing compartment; at least one diaphragm pump connected at a retentate exit end of the filter containing compartment; which diaphragm pump is capable of alternately receiving fluid from the retentate exit end of the filter containing compartment and then expelling the fluid back into the retentate exit end of the filter containing compartment; and at least one fluid harvest port connected to the filter containing compartment for removing filtered fluid from the filter containing compartment;
   b) filtering a fluid by causing fluid to flow from the vessel through the filter containing compartment and then to the diaphragm pump;
   c) causing at least a portion of the fluid to flow from the diaphragm pump through the filter containing compartment;
   d) optionally repeating steps b and c; and
   e) removing the filtered fluid from the filtration system.

30. A fluid filtration system comprising:
   a compartment configured to contain a filter, the compartment comprising a retentate-side inlet and a retentate-side outlet;
   a pump connected in fluid communication with the retentate-side outlet;
   a pump control system configured to operate the pump so that it alternately receives fluid from the retentate-side outlet and expels at least a portion of the fluid back into the retentate-side outlet.

31. A process for filtering comprising:
   supplying a fluid to a compartment containing a filter
   causing at least a portion of the fluid to flow through a retentate side of the compartment to a pump in fluid communication with a retentate-side outlet of the compartment;
   causing at least a portion of the fluid flowed to the pump to flow from the pump back to the retentate-side outlet and through the filter containing compartment; and
   passing at least a portion of the fluid through the filter to form a filtered permeate.

* * * * *